United States Patent [19]

Hashizume et al.

[11] Patent Number: 5,238,818
[45] Date of Patent: Aug. 24, 1993

[54] OXIDIZABLE COLOR PRODUCING REAGENT

[75] Inventors: Kazunari Hashizume; Haruhiko Sugiyama; Mutsuhiro Date, all of Amagasaki, Japan

[73] Assignee: Wako Pure Chemicals Co., Ltd., Osaka, Japan

[21] Appl. No.: 797,836

[22] Filed: Nov. 26, 1991

[30] Foreign Application Priority Data

Nov. 30, 1990 [JP] Japan .................................. 2-329550

[51] Int. Cl.$^5$ .................. C07C 103/44; G01N 33/53; C12Q 1/28
[52] U.S. Cl. ........................................ 435/28; 435/10; 435/14; 435/25; 435/7.94; 564/417; 564/412; 564/442; 558/412; 560/18
[58] Field of Search .................... 435/28, 10, 14, 25, 435/7.94; 560/18; 564/417, 412, 442; 558/412

[56] References Cited

U.S. PATENT DOCUMENTS

| | | | |
|---|---|---|---|
| 4,145,364 | 3/1979 | Mulvey et al. | 260/578 |
| 4,912,258 | 3/1990 | Batz et al. | 564/157 |
| 4,937,186 | 6/1990 | Siddiqi et al. | 435/28 |
| 4,940,660 | 7/1990 | Hirai et al. | 435/7.94 |

FOREIGN PATENT DOCUMENTS 0430847 6/1991 European Pat. Off. .
0430847A1 6/1991 European Pat. Off. .

OTHER PUBLICATIONS

Stedman's Medical Dictionary, 24th Edition, p. 170.

*Primary Examiner*—Michael G. Wityshyn
*Assistant Examiner*—Louise N. Leary
*Attorney, Agent, or Firm*—Armstrong, Westerman, Hattori, McLeland & Naughton

[57] ABSTRACT

This amount of an oxidative substance or a peroxidase-like substance can be determined by using a combined color former comprising 4-aminoantipyrine or a derivative thereof, etc., as a main color former and a p-fluoroaniline derivative or a salt thereof as a color producing component.

10 Claims, 1 Drawing Sheet

OXIDIZABLE COLOR PRODUCING REAGENT

BACKGROUND OF THE INVENTION

This invention relates to a novel p-fluoroaniline derivative or a salt thereof and a process for determining the amount of an oxidative substance or a peroxidase-like substance by using the p-fluoroaniline derivative or salt thereof as a color producing component.

Measurement of living body components, for example, body fluid components such as blood and urine is indispensable for diagnoses of diseases, elucidation of pathosis, and judgement of progress towards recovery because the change of amounts of the living body components is closely related to diseases. There have been developed methods for measurement of great many body fluid components such as cholesterol, triglycerides, glucose, uric acid, phospholipids, bile acid, monoamine oxidase, etc. in blood. It is generally known that these methods are useful for diagnoses of diseases.

As methods for measurement of serum components, so-called "enzymatic methods" have been generalized. In the enzymatic methods, when an objective component is other than enzymes, there is used an enzyme which acts specifically on the objective component. When an objective component is an enzyme, there is used a compound which is a substrate for the enzyme. In each of these cases, enzymatic reaction is carried out and the reaction product is measured, whereby the amount of objective component is determined. Of the enzymatic methods, there are being increased, with development of oxidizable color producing reagents, methods which comprise acting a hydrogen peroxide producing enzyme, for example, an oxidase on an objective component to produce hydrogen peroxide in an amount corresponding to the amount of the objective component, introducing the hydrogen peroxide into a color producing system using peroxidase and an oxidizable color producing reagent as color producing component, carrying out calorimetric determination on the basis of the coloration thus caused, and thereby determining the amount of the objective component. An example of such methods is a method which comprises introducing hydrogen peroxide produced by a combination of cholesterol and cholesterol oxidase; a triglyceride, lipoprotein lipase and glycerol oxidase; uric acid and uricase; or the like into a color producing system using peroxidase (POD) and an oxidizable color producing reagent, measuring absorbance due to the coloration thus caused, and thereby determining the amount of an objective component. Typical examples of the oxidizable color producing reagent used as color producing component in this method are a combination of 4-aminoantipyrine or a derivative thereof and a phenolic compound or an N,N-disubstituted aniline compound; a combination of 3-methylbenzothiazolinone hydrazone (MBTH) and an aniline compound; 2,2'-azino-bis(3-ethylbenzothiazoline-6-sulfonic acid) (ABTS); triphenylmethane series leuco dyes; benzidine derivatives; o-tolidine derivatives; triarylimidazole derivatives; o-phenylenediamine, etc.

These color producing reagents, however, involve various problems. For example, a dye produced from them is faded by the influence of serum components, the dye has an absorption maximum in a short wavelength region and hence tends to be affected by colored components in a sample, such as hemoglobin, bilirubin, etc. in serum and urine, resulting in low reliability of measured values, and the dye gives a low measuring sensitivity because of its small molecular extinction coefficient, so that the color producing reagents can be utilized only for measurement of a few analytes to be measured. Thus, the color producing reagents have been not always satisfactory.

For solving such problems, there has been developed a p-fluoroaniline derivative obtained by introducing a fluoro group into an aniline derivative (Japanese Patent Unexamined Publication No. 60-243050). Moreover, a dye produced from such an existing p-fluoroaniline derivative is somewhat improved in the fading caused by the influence of serum components but are not yet free from the problem that the dye has an absorption maximum in a relatively short wavelength region and hence tends to be affected by colored components in a sample, such as hemoglobin, bilirubin, etc. in serum and urine, resulting in low reliability of measured values. Therefore, there is a desire to seek further improvement in the color producing reagents.

SUMMARY OF THE INVENTION

The present invention was made in consideration of such conditions and is intended to provide a p-fluoroaniline derivative or a salt thereof which is useful as a coupling component of an oxidizable color producing reagent capable of producing a dye which is hardly faded by the influence of components present in body fluids such as serum together with an analyte to be measured, gives a high measuring sensitivity, and has an absorption maximum in a long wavelength region; and a process for high-precision measurement of an oxidizing substance and a peroxidase-like substance by use of the p-fluoroaniline derivative or salt thereof as a color producing component.

This invention provides a p-fluoroaniline derivative represented by the formula [I], or a salt thereof:

wherein $R^1$ and $R^2$ are independently a hydrogen atom, an alkenyl group, or an alkyl group which may have one or more substituents; $R^3$ and $R^4$ are independently an alkoxy group, an alkenyl group, a hydroxyl group, a halogen atom, a sulfonic acid group, a carboxyl group, a nitro group, an aryl group, or an alkyl group which may have one or more substituents; $R^5$ and $R^6$ are independently a hydrogen atom, an alkoxy group, an alkenyl group, or an alkyl group which may have one or more substituents; and each of combinations of $R^1$ and $R^2$, $R^3$ and $R^5$, and $R^4$ and $R^6$ may form a ring by binding of the two to each other.

This invention further provides a process for determination of an oxidative substance and a peroxidase-like substance by use of the p-fluoroaniline derivative or salt thereof as a coupling component of an oxidizable color producing reagent.

DESCRIPTION OF THE PREFERRED EMBODIMENTS

The present inventors earnestly investigated in order to solve the above problems in various oxidizable color producing reagents widely used in the so-called "enzymatic methods". In the investigation, it was found that in the case of using an oxidizable color producing reagent prepared by combining 4-aminoantipyrine, etc. with a p-fluoroaniline type compound obtained by introducing a fluorine atom into an aniline compound which has substituents further introduced at both the 3-position and the 5-position, a dye produced has an absorption maximum in a long wavelength region and is hardly faded by the influence of components present in body fluids such as serum together with an analyte to be measured, as compared with the case of using an aniline compound having no fluorine atom introduced, or a p-fluoroaniline derivative in which no substituent is present at least one of the 3-position and the 5-position, whereby this invention has been accomplished.

The p-fluoroaniline derivative of this invention is represented by the formula [I]:

[I]

wherein $R^1$ and $R^2$ are independently a hydrogen atom, an alkenyl group, or an alkyl group which may have one or more substituents; $R^3$ and $R^4$ are independently an alkoxy group, an alkenyl group, a hydroxyl group, a halogen atom, a sulfonic acid group, a carboxyl group, a nitro group, an aryl group, or an alkyl group which may have one or more substituents; $R^5$ and $R^6$ are independently a hydrogen atom, an alkoxy group, an alkenyl group, or an alkyl group which may have one or more substituents; and each of combinations of $R^1$ and $R^2$, $R^3$ and $R^5$, and $R^4$ and $R^6$ may form a ring by binding of the two to each other. In the formula [I], as the atom or the group which $R^1$ and $R^2$ independently represent, there can be exemplified hydrogen atom, lower alkenyl groups having 2 to 4 carbon atoms [e.g. ethylen alkenyl group (vinyl group), 1-propenyl group, 2-propenyl group (allyl group), isopropenyl group, 2-butenyl group, etc.], and alkyl groups having 1 to 5 carbon atoms (e.g. methyl group, ethyl group, propyl group, butyl group, amyl group, etc.) which may have one or more substituents and may be either linear or branched. The substituents on the alkyl groups include, for example, hydroxyl group, alkoxy groups having 1 to 5 carbon atoms (e.g. methoxy group, ethoxy group, propoxy group, butoxy group and amyloxy group) which may be either linear or branched, sulfo group, carboxyl group, amino group, unsubstituted amido group, substituted amido groups (e.g. acetamido group, propionamido group, etc.), acyl groups (e.g. acetyl group, propionyl group, butyryl group, etc.), and acyloxy groups (e.g. acetyloxy group, ethylcarbonyloxy group, etc.). The alkyl groups may have a plurality of these substituents and may have plural kinds of the substituents. Of these substituents, the sulfo group and carboxyl group may be in the form of a salt (e.g. a salt with an alkali metal such as lithium, sodium, potassium or the like, or an ammonium salt), and the amino group may be in the form of a mineral acid salt (e.g. hydrochloride, sulfate, etc.) or an organic acid salt (e.g. acetate, propionate, etc.). $R^1$ and $R^2$ may bind to each other to form together with N a ring such as morpholine ring, piperazine ring, piperidine ring or the like.

As the atom or the group which $R^3$ and $R^4$ independently represents, there can be exemplified alkoxy groups having 1 to 5 carbon atoms (e.g. methoxy group, ethoxy group, propoxy group, butoxy group and amyloxy group) which may be either linear or branched; lower alkenyl groups having 2 to 4 carbon atoms [e.g. ethenyl group (vinyl group), 1-propenyl group, 2-propenyl group (allyl group), isopropenyl group, 2-butenyl group, etc.]; a hydroxyl group, halogen atoms (e.g. iodine, chlorine, bromine and fluorine); a sulfo group; a carboxyl group; a nitro group; substituted or unsubstituted aryl groups (e.g. phenyl group, naphthyl group, tolyl group, fluorophenyl group, chlorophenyl group, bromophenyl group, iodophenyl group, methoxyphenyl group, hydroxyphenyl group, etc.); and alkyl groups having 1 to 5 carbon atoms (e.g. methyl group, ethyl group, propyl group, butyl group and amyl group) which may be either linear or branched and have one or more substituents. The substituents on the alkyl groups include halogen atoms (e.g. iodine, chlorine, bromine and fluorine) hydroxyl group, etc. Of the above-exemplified groups, the sulfo group and carboxyl groups may be in the form of a salt (e.g. a salt with an alkali metal such as lithium, sodium, potassium or the like, or an ammonium salt).

As the atom or the group which $R^5$ and $R^6$ independently represents, there can be exemplified hydrogen atom, alkoxy groups having 1 to 5 carbon atoms (e.g. methoxy group, ethoxy group, propoxy group, butoxy group and amyloxy group) which may be linear or branched, lower alkenyl groups having 2 to 4 carbon atoms [e.g. ethenyl group (vinyl group), 1-propenyl group, 2-propenyl group (allyl group), isopropenyl group, 2-butenyl group, etc.], hydroxyl group, halogen atoms (e.g. iodine, chlorine, bromine and fluorine), and alkyl groups having 1 to 5 carbon atoms (e.g. methyl group, ethyl group, propyl group, butyl group and amyl group) which may be either linear or branched, and have one or more substituents. The substituents on the alkyl groups include alkoxy groups having 1 to 5 carbon atoms (e.g. methoxy group, ethoxy group, propoxy group, butoxy group and amyloxy group) which may be either linear or branched, etc. $R^3$ and $R^5$, or $R^4$ and $R^6$ may bind to each other to form an aromatic ring.

The p-fluoroaniline derivative of this invention may be in the form of a salt with a mineral acid (e.g. hydrochloric acid, sulfuric acid, etc.) or an organic acid (e.g. acetic acid, propionic acid, etc.).

The p-fluoroaniline derivative represented by the formula [I] of this invention can easily be synthesized, for example, in the following manner. In the following synthetic method, each of $R^1$ and $R^2$ is other than a hydrogen atom in all the formulas.

For example, a compound of the formula [II]:

wherein $R^3$, $R^4$, $R^5$ and $R^6$ are as defined above (hereinafter abbreviated as "compound II") and a compound of the formula [III]:

wherein X is a halogen atom; and R' is an alkyl group, in an amount of 1 to 3 moles, preferably 1 to 1.2 moles, per mole of compound II are dissolved in a solvent such as an alcohol (e.g. methanol, ethanol or isopropanol), a cyclic ether [e.g. 1,4-dioxane or tetrahydrofuran (THF)] or the like, or a mixture of the solvent and water. To the resulting solution was added a caustic alkali (e.g. sodium hydroxide, potassium hydroxide, calcium hydroxide, etc.) or an alkali carbonate (e.g. sodium carbonate, potassium carbonate, calcium carbonate, etc.), which may be in the form of an aqueous solution, in an amount of 1 to 3 equivalents, preferably 1 to 1.5 equivalents, per equivalent of compound [II]. The reaction is carried out at 0° to 120° C., preferably 10° to 100° C., for several hours to several tens hours, after which the reaction product is purified by a conventional method to obtain a compound of the formula [IV]:

wherein R', $R^3$, $R^4$, $R^5$ and $R^6$ are as defined above (hereinafter abbreviated as "compound IV").

Then, a compound of the formula (V):

wherein X' is a halogen atom; and $R^2$ is as defined above, is reacted with compound [IV] in an amount of 1 to 3 moles, preferably 1 to 1.2 moles, per mole of compound [IV] under the same reaction conditions as for the above reaction, namely, it is reacted with compound [IV] in a solvent such as an alcohol solvent, 1,4-dioxane, THF or the like at 10° to 100° C. for several hours to several tens hours. Thereafter, the reaction product is purified by a conventional method to obtain a compound of the formula [VI]:

wherein R', $R^2$, $R^3$, $R^4$, $R^5$ and $R^6$ are as defined above (hereinafter abbreviated as "compound VI").

Subsequently, for example, a fluorinating agent such as an N-fluoropyridinium salt (e.g. N-fluoro-2,4,6-trimethylpyridinium triflate, N-fluoropyridinium triflate, N-fluoro-3,5-dichloropyridinium triflate, etc.) or the like is reacted with compound [VI] in an amount of 1 to 3 moles, preferably 1 to 1.2 moles, per mole of compound VI in a solvent such as an aromatic hydrocarbon (e.g. benzene, toluene, xylene, etc.), an ether (e.g. diethyl ether, diisopropyl ether, THF, 1,4-dioxane, etc.), a halogenated hydrocarbon (e.g. chloroform, dichloromethane, 1,2-dichloroethane, etc.), dimethylformamide or the like (all of which are preferably dry) at 0° to 150° C., preferably 20° to 120° C., for several hours to several tons hours. The reaction product is then purified by a conventional method to obtain a compound of the formula [VII]:

wherein R', $R^2$, $R^3$, $R^4$, $R^5$ and $R^6$ are as defined above (hereinafter abbreviated as "compound VII").

Next, an inorganic or organic alkali (e.g. sodium hydroxide, potassium hydroxide, sodium methylate, sodium ethylate, etc.) is reacted with compound [VII] in an amount of 1 to 3 moles, preferably 1 to 1.2 moles, per mole of compound VII in a solvent such as methanol, ethanol or the like at 0° to 150° C., preferably 20° to 60° C., for one to several hours. The reaction product is then purified to obtain a compound of the formula [VIII]:

wherein $R^2$, $R^3$, $R^4$, $R^5$ and $R^6$ are as defined above (hereinafter abbreviated as "compound VIII").

Then, a compound of the formula [IX]:

wherein X" is a halogen atom; and $R^1$ is as defined above, is reacted with compound [VIII] in an amount of 1 to 3 moles, preferably 1 to 2 moles, per mole of compound [VIII] in a solvent such as an alcohol (e.g. methanol, ethanol, isopropanol, etc.), a cyclic ether (e.g. 1,4-dioxane or THF) or a mixture of any of them and water at 0° to 120° C., preferably 50° to 100° C., for several hours to several tens hours in the presence of a caustic alkali (e.g. sodium hydroxide, potassium hydroxide, calcium hydroxide, etc.) or an alkali carbonate (e.g. sodium carbonate, potassium carbonate, calcium carbonate, etc.). Thereafter, the reaction product is purified by a conventional method to obtain the desired p-fluoroaniline derivative represented by the formula [I] of this invention.

In the above reactions, the compound of the formula [VIII] can be obtained also by the method described below and the product obtained by this method may also be used.

A 4-fluoronitrobenzene derivative of the formula [II']:

wherein $R^3$, $R^4$, $R^5$, and $R^6$, are as defined above, is obtained by nitrating a corresponding fluorobenzene derivative according to the method described in J. Chem. Soc., 1963, 5554.

Then, the 4-fluoronitrobenzene derivative is reduced by a conventional method for reducing an aromatic nitro compound, for example, catalytic reduction to obtain a compound of the formula [II"]:

wherein $R^3$, $R^4$, $R^5$, and $R^6$, are as defined above (hereinafter abbreviated as "compound II'''"). Thereafter, a compound of the formula [V]:

wherein X' and $R^2$ are as defined above, is reacted with compound [II'''] under the same reaction conditions as the above conditions for reacting a compound of the formula V] with comound [IV], whereby the compound of the formula [VIII] can be obtained.

The p-fluoroaniline derivative of this invention can be obtained also by fluorinating, for example, a compound of the formula [X]:

wherein $R^1$, $R^2$, $R^3$, $R^4$, $R^5$ and $R^6$ are as defined above, under the same reaction conditions as the above conditions for fluorinating compound [VI] into compound [VII].

For synthesizing a compound of the formula [I] in which at least either $R^1$ or $R^2$ is a hydrogen atom, it is of course sufficient that of the reaction steps in the above synthetic method, only necessary steps are carried out.

As compound [II] used for producing the p-fluoroaniline derivative of this invention, a commercial one may be used as it is. When compound [II] is not commercially available, there may be used as compound [II] an aniline derivative obtained by nitration and then reduction of a benzene derivative corresponding to compound II by a conventional method.

Exactly the same applies to Compound [X].

The p-fluoroaniline derivative or salt thereof of this invention is very stable in water or a buffer solution containing a surfactant dissolved therein. When a combination of the p-fluoroaniline derivative or salt thereof and a main color former (e.g. 4-aminoantipyrine or a derivative thereof, phenylenediamine, or MBTH) is oxidized by an oxidizing agent (for example, when the combination is oxidized with hydrogen peroxide in the presence of peroxidase), the combination quantitatively forms a dye having an excellent coloration stability. Moreover, this dye has excellent properties in that it has an absorption maximum in a long wavelength region and is hardly faded by the influence of components present together with an analyte to be measured in a body fluid such as serum, urine or the like which is used as a sample, as compared with a dye formed in the same manner as above by using a conventional p-fluoroaniline derivative having no substituent at both the 3-position and the 5-position, or having a substituent only at either the 3-position or the 5-position. Therefore, the p-fluoroaniline derivative or salt thereof of this invention can be effectively used as a coupling compound of a color producing reagent in quantitation of an oxidizing agent or quantitation of a peroxidase-like substance. The p-fluoroaniline derivative or salt thereof can be effectively used particularly as a coupling component of a color producing reagent in quantitation of trace components in samples derived from living bodies, for example, serum, plasma and urine, which comprises introducing hydrogen peroxide produced by enzymatic reaction into a color producing system in the presence of peroxidase, and carrying out calorimetric determination on the basis of the coloration thus caused.

That is, the process for determining the amount of an oxidative substance of this invention can be particularly effectively used as a process for measuring a trace component in a sample derived from a living body, by acting an oxidase on a substrate or a substance produced by enzymatic reaction, and determining hydrogen peroxide produced, namely, as a process for measuring the substrate or enzymatic activity.

Trace components in samples derived from living bodies which can be measured by the process of this invention include, for example, cholesterol, glucose, glycerol, triglycerides, free fatty acids, uric acid, phospholipids, bile acid, monoamine oxidase, guanase, choline esterase, etc. The trace components are not limited thereto, and the process of this invention permits determination of all living body components which can be measured by determining quantitatively hydrogen peroxide produced by enzymatic reaction.

The measuring process of this invention is characterized by using a combination of a main color former (e.g. 4-aminoantipyrine or a derivative thereof, phenylenediamine, or MBTH) and the p-fluoroaniline derivative or salt thereof, as a color producing reagent (an oxidizable color producing reagent) and able to use other conditions employed in a known enzymatic method using a hydrogen peroxide producing enzyme.

Although the concentrations of the main color former and the p-fluoroaniline derivative or salt thereof of this invention used in the color producing reagent are not critical, there are used in proper combination the main color former usually in a concentration range of 50 to 2000 μmol/liter, preferably 100 to 1,000 μmol/liter, and the p-fluoroaniline derivative or salt thereof of this invention usually in a concentration range of 100 to 2,000 μmol/liter, preferably 500 to 1,000 μmol/liter.

In determining a living body component quantitatively by the process of this invention, the kinds and the using amounts of the oxidase used as an enzyme for producing hydrogen peroxide, other enzymes used for other purposes, a substrate which participates in the enzymatic reaction, and other substances may be properly chosen depending on an analyte to be measured, in accordance with a per se well-known process for measuring a living body component by use of an oxidizable color reagent. The origin and source of peroxidase or peroxidase-like substance used in determination of hydrogen peroxide by the process of this invention are not critical. As the peroxidase or peroxidase-like substance, those derived from plants, animals and microorganisms can be used singly or optionally in combination of two or more thereof. The using amount of the peroxidase or peroxidase-like substance is not critical and is properly determined depending on purposes.

Quantitation of a living body component by the process of this invention is carried out usually at pH 4.0–10.0, preferably pH 6.0–8.0. As a buffer used in the quantitation, there can be exemplified buffers usually used in the art, for example, phosphates, citrates, borates, carbonates, tris(hydroxymethyl)aminomethane and Good's buffer. The buffer is not particularly limited thereto.

The p-fluoroaniline derivative of this invention can be effectively used in combination with a main color former, for determining an oxidative substance such as hydrogen peroxide, periodic acid or the like quantitatively. Combined use of the p-fluoroaniline derivative, a main color former and hydrogen peroxide permits quantitation of a peroxidase-like substance. The peroxidase-like substance include peroxidase itself and heme compounds such as hemoglobin, etc.

That is, the p-fluoroaniline derivative or salt thereof of this invention can be effectively used, for example, for enzyme immunoassay using peroxidase as a labeling compound and measurement of hemoglobin in serum of use of an oxidative substance such as hydrogen peroxide, sodium peroxide or the like.

This invention is applicable also to dry chemistry.

More concretely, the trace components present in living body samples can be measured as follows:

(1) Cholesterol
(Reactions)

chloresterol ester + H$_2$O $\xrightarrow{\text{CEH}}$ cholesterol cholesterol + O$_2$ $\xrightarrow{\text{COD}}$ Δ$^4$-cholestenone + H$_2$O$_2$ H$_2$O$_2$ + 4-aminoantipyrine + P-fluoroaniline derivative $\xrightarrow{\text{POD}}$ color development (Reagent solution)
0.1 M tris-maleate buffer (pH 7.0)

| | | |
|---|---|---|
| cholesterol esterase (CEH) | 0.1–10 u/ml | (3.0 u/ml) |
| cholesterol oxidase (COD) | 0.1–10 u/ml | (0.4 u/ml) |
| peroxidase (POD) | 0.3–30 u/ml | (5 u/ml) |
| Triton X-100 | 0.05–0.2% | (0.1%) |
| 4-aminoantipyrine | 0.5–5 mM | (3 mM) |
| p-fluoroaniline derivative | 50–1000 μM | (500 μM) |
| ascorbate oxidase | 3–20 u/ml | (5 u/ml) |

(Procedure)

Sample + Reagent solution $\xrightarrow{\text{(incubate)}}$ color development
(10 μl)      (3 ml)      (measurement)

(1') Free cholesterol
(Reactions)

Cholesterol + O$_2$ $\xrightarrow{\text{COD}}$ Δ$^4$-cholestenone + H$_2$O$_2$

H$_2$O$_2$ + 4-aminoantipyrine + p-fluoroaniline derivative $\xrightarrow{\text{POD}}$ color development (Reagent solution)
The same as mentioned above except for not containing CEH.
(Procedure)
The same as mentioned above (2) Glucose
(Reactions)

glucose + O$_2$ + H$_2$O $\xrightarrow{\text{GOD}}$ H$_2$O$_2$ + gluconic acid

H$_2$O$_2$ + 4-aminoantipyrine + p-fluoroaniline derivative $\xrightarrow{\text{POD}}$ color development (Reagent solution)
0.1 M phosphate buffer (pH 7.0)

| | | |
|---|---|---|
| glucose oxidase (GOD) | 10–100 u/ml | (30 u/ml) |
| peroxidase (POD) | 0.3–20 u/ml | (5 u/ml) |
| 4-aminoantipyrine | 0.5–5 mM | (3 mM) |
| p-fluoroaniline derivative | 50–1000 μM | (500 μM) |
| [mutarotase | 0.02–0.5 u/ml | (0.067 u/ml] |
| ascorbate oxidase (AOD) | 3–20 u/ml | (5 u/ml) |

(Procedure)

Sample + Reagent solution $\xrightarrow{\text{(incubate)}}$ color development
(10 μl)      (3 ml)      (measurement)

(3) Triglyceride
(Reactions)

triglyceride + 3H$_2$O $\xrightarrow{\text{LPL}}$ glycerol + 3 fatty acids glycerol + ATP $\xrightarrow{\text{GK}}$ glycerol-3-phosphate + ADP glycerol-3-phosphate + O$_2$ $\xrightarrow{\text{GPO}}$ dihydroxyacetone phosphate + H$_2$O$_2$
H$_2$O$_2$ + 4-aminoantipyrine + p-fluoroaniline derivative $\xrightarrow{\text{POD}}$ color development (Reagent solution)
tris buffer (pH 6.5)

-continued

| | | |
|---|---|---|
| glycerol kinase (GK) | 0.5–15 u/ml | (5 u/ml) |
| glycerol-3-phosphate oxidase (GPO) | 1–20 u/ml | (5 u/ml) |
| peroxidase (POD) | 0.3–30 u/ml | (5 u/ml) |
| magnesium acetate | 1–7 mM | (2mM) |
| adenosine-5'-triphosphate | 0.5–30 mM | (2 mM) |
| lipoprotein lipase (LPL) | 10–150 u/ml | (60 u/ml) |
| 4-aminoantipyrine | 0.5–5 mM | (3 mM) |
| p-fluoroaniline derivative | 50–1000 μM | (500 μM) |
| ascorbate oxidase (AOD) | 3–20 u/ml | (5 u/ml) |

(Procedure)

Sample + Reagent solution $\xrightarrow{\text{(incubate)}}$ color development (measurement)
(10 μl)         (3 ml)

(3') Glycerol
(Reactions)

glycerol + ATP $\xrightarrow{GK}$ glycerol-3-phosphate + ADP glycerol-3-phosphate + $O_2$ $\xrightarrow{GPO}$ dihydroxyacetone phosphate + $H_2O_2$ $H_2O_2$ + 4-aminoantipyrine + p-fluoroaniline derivative $\xrightarrow{POD}$ color development (Reagent solution)
The same as mentioned above except for not containing LPL.
(Procedure)
The same as mentioned above (4) Non-esterified fatty acid
(Reactions)

RCOOH + ATP + CoA $\xrightarrow{ACS}$ Acryl-CoA—AMP + PPI

Acryl-CoA + $O_2$ $\xrightarrow{ACOD}$ 2,3-trans-Enoyl-CoA + $H_2O_2$ $H_2O_2$ + 4-aminoantipyrine + p-fluoroanionic derivative $\xrightarrow{POD}$ color development (Reagent solution)
PIPES-NaOH buffer (pH 6.9)

| | | |
|---|---|---|
| acryl CoA-synthesizer (ACS) | 0.05–5 u/ml | (0.1 ul) |
| Acryl CoA-oxidase (A COD) | 1–15 u/ml | (3 u/ml) |
| coenzyme A (CoA) | 0.2–5 mg/ml | (0.5 mg/ml) |
| Peroxidase (POD) | 0.3–30 u/ml | (5 u/ml) |
| ascorbate oxidase (AOD) | 3–20 u/ml | (5 u/ml) |
| 4-aminoantipyrine | 0.5–5 mM | (3 mM) |
| p-fluoroaniline derivative | 50–100 μM | (500 μM) |
| adenosine-5'-phosphate (ATP) | 1–15 mg/ml | (3 mg/ml) |
| magnesium chloride | 0.5–5 mM | (2 mM) |
| Emulgen 913 (polyoxyethylene nonyl phenol ether) | 0.05–0.4% | (0.2%) |

(Procedure)

Sample + Reagent solution $\xrightarrow{\text{(incubate)}}$ color development (measurement)
(20 μl)         (3 ml)

(5) Uric acid
(Reactions)

uric acid + $O_2$ + $2M_2O$ $\xrightarrow{\text{uricase}}$ allantoin + $CO_2$ + $H_2O_2$ $H_2O_2$ + 4-aminoantipyline + p-fluoroaniline derivative $\xrightarrow{POD}$ color development (Reagent solution)
PIPES-NaOH buffer (pH 6.4)

| | | |
|---|---|---|
| uricase | 0.5–10 u/ml | (2 u/ml) |
| peroxidase (POD) | 0.3–30 u/ml | (10 u/ml) |
| ascorbate oxidase (AOD) | 1–20 u/ml | (2 u/ml) |
| 4-aminoantipyrine | 0.5–5 mM | (3 mM) |
| p-fluoroaniline derivative | 50–1000 μM | (500 μM) |

(Procedure)

Sample + Reagent solution $\xrightarrow{\text{(incubate)}}$ color development (measurement)
(10 μl)         (3 ml)

(6) Phospholipids
(Reactions)

phospholipids $\begin{pmatrix} \text{lecithin} \\ \text{sphingosine} \\ \text{lysolecithin} \end{pmatrix}$ + $H_2O$ $\xrightarrow{\text{phospholipase}}$ choline + $\begin{pmatrix} \text{phosphatidic acid} \\ \text{N-acylsphingosyl phosphate} \\ \text{lysophosphatidic acid} \end{pmatrix}$ choline $\xrightarrow{\text{choline oxidase}}$ betaine + $2H_2O_2$ $H_2O_2$ + 4-aminoantipyrine + p-fluoroaniline derivative $\xrightarrow{POD}$ color development (Reagent solution)
tris buffer (pH 7.7)

| | | |
|---|---|---|
| phospholipase D | 0.4–10 u/ml | (0.7 u/ml) |
| choline oxidase | 1–20 u/ml | (3 u/ml) |
| peroxidase (POD) | 0.3–30 u/ml | (5 u/ml) |
| ascorbate oxidase | 2–20 u/ml | (5 u/ml) |
| 4-aminoantipyrine | 0.5–5 mM | (3 mM) |
| p-fluoroaniline derivative | 50–1000 μM | (500 μM) |

(Procedure)

Sample + Reagent solution $\xrightarrow{\text{(incubate)}}$ color development (measurement)
(10 μl)         (3 ml)

(7) Monoamine oxidase (MAO)
(Reactions)

$CH_2=CHCH_2CH_2$ + $O_2$ + $H_2O$ $\xrightarrow{MAO}$
(allylamine)

$CH_2=CHCHO$ + $NH_3$ + $H_2H_2$
(acrolein)

$H_2O_2$ + 4-aminoantipyrine + p-fluoroaniline derivative $\xrightarrow{POD}$ color development (Reagent solution)

| 25 mM PIPES-NaOH buffer (pH 6.75) | | |
|---|---|---|
| allylamine | 10–100 mM | (25 mM) |
| peroxidase (POD) | 0.3–30 u/ml | (5 u/ml) |
| ascorbate oxidase | 2–20 u/ml | (5 u/ml) |
| 4-aminoantipyrine | 0.5–5 mM | (3 mM) |
| p-fluoroaniline derivative | 50–1000 μM | (500 μM) |

(Procedure)

Sample + Reagent solution $\longrightarrow$ rate assay
(100 μl)    (3 ml)    (incubate)

(8) Transaminase (A) Glutamic oxaloacetic transaminase (GOT)

L-aspartic acid + α-ketoglutaric acid $\underset{\longrightarrow}{\overset{GOT}{\longleftarrow}}$ oxaloacetic acid + glutamic acid oxaloacetic acid $\xrightarrow{OAC}$ pyruvic acid + $CO_2$ (B) cultamic pyruvic transaminase L-alanine + α-ketoglutaric acid $\underset{\longrightarrow}{\overset{GPT}{\longleftarrow}}$ pyruvic acid + glutamic acid pyruvic acid + $HOPO_3^{2-}$ + $O_2$ $\xrightarrow{POP}$ acetyl phosphate + $CO_2$ + $H_2O_2$ $H_2O_2$ + 4-aminoantipyrine + fluoroaniline derivative $\xrightarrow{POD}$ color development (Reagent solution)

(A) GPT
First solution:

| phosphate buffer (pH 7.0) | | |
|---|---|---|
| pyruvate oxidase (POP) | 1–10 u/ml | (6 u/ml) |
| peroxidase (POD) | 0.2–20 u/ml | (10 u/ml) |
| thiamine pyrophosphate (TPP) | 0.01–0.5% | (0.06%) |
| flavin-adenine dinucleotide (FAD) | 0.001–0.1% | (0.002%) |
| magnesium acetate | 1–10 mM | (9 mM) |
| catalase | 50–500 u/ml | (100 u/ml) |

Second solution:

| phosphate buffer (pH 7.0) | | |
|---|---|---|
| DL-alanine | 200–800 mM | (700 mM) |
| α-ketoglutamic acid | 10–50 mM | (35 mM) |
| 4-aminoantipyrine | 0.5–5 mM | (5 mM) |
| p-fluoroaniline derivative | 50–1000 μM | (500 μM) |
| $NaN_3$ | 0.1–0.4% | (0.2%) |

Third solution (Reaction stopper):

| 0.1 M citrate buffer (pH 6.8) | | |
|---|---|---|
| sodium dodecylbenzene-sulfonate | 0.1–1% | (0.5%) |
| EDTA.2Na | 0.5–2 mM/l | (1 mM/l) |

(Procedure)

Sample + 1st reagent solution $\xrightarrow{\text{(incubate)}}_{(37°\text{ C., 5 min)}}$ +
(20 μl)   (0.5 ml)

2nd reagent solution $\xrightarrow{\text{incubate}}_{(37°\text{ C., 20 min)}}$ +
(0.5 ml)

reaction stopper $\longrightarrow$ color development
(2 ml)   (measurement)

(B) GOT
First solution:

| Phosphate buffer (pH 7.0) | | |
|---|---|---|
| pyruvate oxidase (POP) | 1–10 u/ml | (6 u/ml) |
| peroxidase (POD) | 0.2–20 u/ml | (10 u/ml) |
| thiamine pyrophosphate (TPP) | 0.01–0.5% | (0.06%) |
| flavin-adenine dinucleotide (FAD) | 0.001–0.1% | (0.002%) |
| magnesium acetate | 1–10 mM | (9 mM) |
| catalase | 50–500 u/ml | (100 u/ml) |
| oxaloacetate decarboxylase (OAC) | 1–50 u/ml | (20 u/ml) |

Second solution:

| phosphate buffer (pH 7.0) | | |
|---|---|---|
| L-aspartic acid | 100–600 mM | (400 mM) |
| α-ketoglutaric acid | 10–50 mM | (35 mM) |
| 4-aminoantipyrine | 0.5–5 mM | (3 mM) |
| p-fluoroaniline derivative | 50–1000 μM | (500 μM) |
| $NaN_3$ | 0.1–0.4% | (0.2%) |

Third solution (Reaction Stopper):

| 0.1 M citrate buffer (pH 6.8) | | |
|---|---|---|
| sodium dodecyl-benzenesulfonate | 0.1–1% | (0.5%) |
| EDTA.2Na | 0.5–2 mM/l | (1 mM/l) |

(Procedure)

Sample + 1st reagent solution $\xrightarrow{\text{(incubate)}}_{(37°\text{ C., 5 min)}}$
(20 μl)   (0.5 ml)

2nd reagent solution $\xrightarrow{\text{(incubate)}}_{(37°\text{ C., 20 min)}}$ +
(0.5 ml)

stopper reaction $\longrightarrow$ color development
(2 ml)   (measurement)

(9) Creatine
(Reactions)

creatine + $H_2O$ $\xrightarrow{\text{creatine amidinohydrate}}$ sarcosine + urea sarcosine + $H_2O$ + $O_2$ $\xrightarrow{\text{sarcosine oxidase}}$ $H_2O_2$ + HCHO + glycine $H_2O_2$ + 4-anilinoantipyrine + p-fluoroaniline $\xrightarrow{POD}$ color development (Reagent solution)
First solution:

| 50 mM phosphate buffer (pH 8.0) | | |
|---|---|---|
| sarcosine oxidase | 1–40 u/ml | (20 u/ml) |
| peroxidase | 0.2–20 u/ml | (10 u/ml) |
| catalase | 50–400 u/ml | (100 u/ml) |

Second solution:

| 50 mM phosphate buffer (pH 8.0) | | |
|---|---|---|
| creatine amidinohydrase | 1–100 u/ml | (50 u/ml) |
| $NaN_3$ | 0.1–0.4% | (0.2%) |
| 4-aminoantipyrine | 0.5–5 mM | (3 mM) |
| p-fluoroaniline derivative | 50–1000 μM | (500 μM) |

(Procedure)

Sample + 1st reagent solution $\xrightarrow{\text{(incubate)}}$ +
(50 μl)   (1 ml)

-continued

2nd reagent solution (1 ml) $\xrightarrow[(37° C., 5-10 \text{ min})]{\text{(incubate)}}$ color development (measurement)

(10) Bile acids
(Reactions)

3α-hydroxysteroid + NAD+ $\xrightarrow{3\alpha\text{-NSD}}$ 3-ketosteroid + NADH + H+

NADH + 4-aminoantipyrine + p-fluoroaniline derivative $\xrightarrow[Mn^{2+}]{POD}$ color development (Reagent solution)
50 mM tris-HCl buffer (pH 8.0)

| | | |
|---|---|---|
| 3α-hydroxysteroid dehydrogenase (3α-HSD) | 0.005–1 u/ml | (0.01 u/ml) |
| nicotinamide adenine dinucleotide (DNA) | 0.1–3 mM | (1 mM) |
| MnCl₂ | 0.2–5 mM | (1 mM) |
| peroxidase (POD) | 0.2–30 u/ml | (3 u/ml) |
| 4-aminoantipyrine | 0.5–5 mM | (3 mM) |
| p-fluoroaniline derivative | 50–1000 μM | (500 μM) |

(Procedure)

Sample + Reagent solution $\xrightarrow[(37° C., 20 \text{ min})]{\text{(incubate)}}$
(50 μl)    (3 ml)

color development
(measurement)

(11) Peroxidase
(Reaction)

4-aminoantipyrine + P-fluoroaniline derivative +

H₂O₂ $\xrightarrow{POD}$ color development
(substrate)

(Reagent solution)
50 mM phosphate buffer (pH 6.0)

| | | |
|---|---|---|
| 4-aminoantipyrine | 0.5–5 mM | (3 mM) |
| p-fluoroaniline derivative | 50–1000 μM | (500 μM) |
| H₂O₂ | 0.02–0.3 mM | (0.1 mM) |

(Procedure)

Sample + Reagent solution $\xrightarrow{\text{(incubate)}}$ color
(10 μl)    (3 ml)                          development
                                           (measurement)

The POD activity can be obtained by measuring a changing rate per unit time. This procedure can also be applied to the determination of hemoglobin.

This invention is explained below in further detail with reference to Examples and Reference Examples, which are not by way of limitation but by way of illustration.

EXAMPLE 1

Synthesis of N-ethyl-N-(2-hydroxyethyl)-3,5-dimethyl-4-fluoroaniline (present invention compound [1])

In 120 ml of nitric acid was dissolved 120 g of 3,5-dimethyl-4-fluorobenzene (mfd. by Columbia Organic Chemical Co., Inc.) at −10° C. over a period of 1 hour, after which the temperature was adjusted to −15° C. and the reaction was carried out with stirring for another 1 hour. After completion of the reaction, the reaction solution was poured onto ice and the yellow crystals thus precipitated were collected by filtration and subjected to distillation at atmospheric pressure to obtain 40 9 of 3,5-dimethyl-4-fluoro-1-nitrobenzene as distillate having a boiling point of 111°–112° C.

In 3 liters of methanol was dissolved 15 g of this 3,5-dimethyl-4-fluoro-1-nitrobenzene, and the resulting solution was treated with nitrogen to replace the air, after which 10 g of palladium carbon was added and catalytic reduction with hydrogen gas was carried out. After completion of the reaction, the insoluble materials were filtered off and the filtrate was concentrated to obtain 12.3 g of 3,5-dimethyl-4-fluoroaniline.

In a mixed solution of 100 ml of ethanol and 60 ml of a 2N-NaOH solution were dissolved 12.3 g of the 3,5-dimethyl-4-fluoroaniline and 81 g of 2-chloroethanol, and the resulting solution was subjected to reaction with refluxing for 3 hours. After completion of the reaction, the ethanol was distilled off and the residue was extracted with ethyl acetate, after which the extract was washed with water, dried and then concentrated to obtain 14 g of crude N-(2-hydroxyethyl)-3,5-dimethyl-4-fluoroaniline. Subsequently, this crude compound was dissolved in 100 ml of isopropanol, followed by adding thereto 15 g of iodoethane and 20 g of potassium carbonate, and the reaction was carried out with refluxing for 5 hours. After completion of the reaction, the solvent was distilled off and the residue was extracted with ethyl acetate, and the extract was washed with water, dried and then concentrated to obtain 16 g of a crude product of the desired compound. The crude product was purified by a column chromatography (packing; Wakogel C-300, a registered trade name, mfd. by Wako Pure Chemical Industries, Ltd., eluent: ethyl acetate : n-hexane =1 : 2) to obtain 9.5 g of oily N-ethyl-N-(2-hydroxyethyl)-3,5-dimethyl-4-fluoroaniline.

IR (Neat): 2900–2980 cm$^{-1}$(CH), 1600 cm$^{-1}$ (Aromatic CH), 1500 cm$^{-1}$ (Aromatic CH), 1200 cm$^{-1}$ (CO)

m.p.: 330°–335° C.

Elementary analysis values ($C_{12}H_{18}FNO$): Calculated (%): C. 68.22, H 8.59, N 6.63, Found (%): C. 68.62, H 8.79, N 6.24.

EXAMPLE 2

Synthesis of N-ethyl-N-(2-hydroxy-3-sulfopropyl)-3,5-dimethoxy-4-fluoroaniline (present inventive compound [2])

In a mixed solution of 450 ml of 1,4-dioxane and 230 ml of water was dissolved 34.7 g of 3,5-dimethoxyaniline (mfd. by Aldrich Chemical Co.), and the resulting solution was cooled to 0° C., after which 390 ml of 1 N NaOH and 30 g of ethyl carbonate were added, and the reaction was carried out at 20° C. for 20 hours. After completion of the reaction, the reaction solution was acidified with 1 N HCl and extracted with ethyl acetate. The organic layer thus obtained was washed with water and dried over anhydrous magnesium sulfate, after which the solvent was distilled off. Then, the resulting residue was dissolved in 300 ml of THF, followed by adding thereto 9.07 g of sodium hydroxide and 35.4 g of iodoethane, and the reaction was carried out at 40° C. for 2 hours. After completion of the reaction, the reaction solution was concentrated and water was added to the residue, and the resulting mixture was extracted with 500 ml of 1,2-dichloroethane. The extract was sufficiently dried over anhydrous magnesium sulfate, after which 64.8 g of N-fluoro-2,4,6-trimethylpyridinium triflate (mfd. by Onoda Cement Co., Ltd.) was added and the resulting mixture was subjected to reaction with stirring at 100° C. for 8 hours. After completion of the reaction, the solvent was distilled off and water was added to the residue, after which the resulting mixture was extracted with dichlorometahne and the organic layer thus obtained was dried over anhydrous magnesium sulfate. After the drying, the solvent was distilled off and the resulting residue was dissolved in 200 ml of methanol, followed by adding thereto 230 ml of a 1 N NaOH solution. An elimination reaction of carbonate ester was carried out at 50° C. for 2 hours. Then, the reaction solution was treated by a column chromatography [packing; Wakogel C-300 (a registered trade name, Wako Pure Chemical Industries, Ltd.), eluent; hexane : ethyl acetate =4 : 1] to obtain a fraction containing N-ethyl-3,5-dimethoxy-4-fluoroaniline. The solvent was distilled off from this fraction and the residue was dissolved in a mixed solution of 24 ml of water and 24 ml of isopropanol, followed by adding thereto 24 ml of 1 N NaOH solution an 4.7 g of sodium 3-chloro-2-hydroxypropylsulfonate (mfd. by Tokyo Kasei Kogyo Co., Ltd.). The reaction was carried out with stirring at 80° C. for 5 hours. After completion of the reaction, the solvent was distilled off, and the residue was washed with ether and then recrystallized from water to obtain 6.59 g of white crystals of N-ethyl-N-(2-hydroxy-3-sulfopropyl)-3,5-dimethoxy-4-fluoroaniline.

IR (KBr): 3400 cm$^{-1}$ (CH), 3050-2800 cm$^{-1}$ (CH), 1200 cm$^{-1}$ (SO$_2$), 1050 cm$^{-1}$ (CO).

m.p.: 210°–215° C.

Elementary analysis values (C$_{13}$H$_{19}$FNNaO$_4$S): Calculated (%): C. 47.70, H 5.85, N 4.28, Found (%): C. 47.37, H 5.65, N 4.02.

REFERENCE EXAMPLE 1

Measurement of Properties of Compounds of This Invention (1) Measurement of Molecular Extinction Coefficient and Absorption Maximum (λmax)

Color Producing Solution

A color producing solution was prepared by dissolving each of predetermined compounds of this invention, 4-aminoantipyrine and peroxidase in 50 mM piperazine-N,N'-bis(2-ethanesulfonic acid) (PIPES)-sodium hydroxide buffer (pH 7.0) to concentrations of 5.0 mM, 0.5 mM and 1 u/ml, respectively.

Procedure

To 3 ml of the color producing solution prepared by use of each compound of this invention was added 20 µl of a 1 mM aqueous hydrogen peroxide solution, followed by thorough mixing, and the resulting solution was incubated at 37° C. for 5 minutes. Absorption curve of the reaction solution was measured, and λmax and absorbance at λmax, Es, were determined.

As a control standard solution for measuring the absorption curve and λmax, there was used a solution obtained by adding 20 µl of purified water to 3 ml of each color producing solution, mixing them thoroughly, and incubating the resulting solution at 37° C. for 5 minutes.

Molecular extinction coefficient was calculated by the equation shown below, by using an Es value obtained for each color producing solution and absorbance E$_{OH}$ at 505 nm obtained by the above procedure, except for using 50 mM PIPES-sodium hydroxide buffer (pH 7.0) containing 50 mM each of 4-aminoantipyrine and phenol and 1 U/ml of peroxidase, in place of each color producing solution.

Molecular extinction coefficient
$= (Es + E_{OH}) \times 5 \times 10^3$

The results obtained are shown in Table 1-1.

(2) Measurement of the Influence of Serum Components

With 3 ml of each color producing solution prepared in (1) were mixed 20 µl of pooled normal human serum and then 20 µl of a 1 mM aqueous hydrogen peroxide solution, and the resulting mixture was incubated at 37° C. for 5 minutes. Absorbance at λmax of the reaction solution, E$_{ef}$, was measured. Absorbance E$_{std}$ was obtained by carrying out the same procedure as above by use of the same color producing solution as above, except for using purified water in place of the pooled normal human serum.

The value "a" which is an indication of the influence of serum components was calculated by substituting the thus obtained E$_{ef}$ and E$_{std}$ values in the following equation:

$a = (E_{ef} + E_{sed}) \times 100$

The influence of serum components were expressed as follows on the basis of value "a", −: value "a" was 0 to 1.
±: value "a" was 1 to 2.
++: value "a" was 3 or more.

The results obtained are also shown in Table 1-1.

Present inventive compounds 3 to 5 in Table 1-1 were synthesized according to the synthetic method described in Example 1 or 2.

For comparison, the results of measuring properties of known p-fluoroaniline derivatives in the same manner as above are shown in Table 1-2 and Table 1-3.

TABLE 1-1

| Compound No. | Structural formula | Molecular extinction coefficient (× 10$^3$) | λmax (mn) | Influence of serum components |
|---|---|---|---|---|
| Compounds of present invention | | | | |

TABLE 1-1-continued

| Compound No. | Structural formula | Molecular extinction coefficient ($\times 10^3$) | λmax (mn) | Influence of serum components |
|---|---|---|---|---|
| 1 | 4-F, 3,5-di-$CH_3$ phenyl-N($C_2H_5$)($C_2H_4OH$) | 22 | 610 | − |
| 2 | 4-F, 3,5-di-$OCH_3$ phenyl-N($C_2H_5$)($CH_2CH(OH)CH_2SO_3Na$) | 22 | 595 | − |
| 3 | 4-F, 3,5-di-$CH_3$ phenyl-N($C_2H_5$)($CH_2CH_2CH_2SO_3Na$) | 25 | 605 | − |
| 4 | 4-F, 3,5-di-$CH_3$ phenyl-N($C_2H_5$)($CH_2CH_2COONa$) | 22 | 610 | − |
| 5 | 4-F, 3,5-di-$OCH_3$ phenyl-N($C_2H_5$)($CH_2CH_2$-NH-COCH$_3$) | 21 | 590 | + |

TABLE 1-2

| Compound No. | Structural formula | Molecular extinction coefficient ($\times 10^3$) | λmax (mn) | Influence of serum components |
|---|---|---|---|---|
| Comparative Example | | | | |
| 1 | 4-F, 3-$CH_3$ phenyl-N($C_2H_5$)($C_2H_4OH$) | 29 | 550 | + |
| 2 | 4-F, 3-$OCH_3$ phenyl-N($C_2H_5$)($CH_2CH(OH)CH_2SO_3Na$) | 25 | 540 | + |
| 3 | 4-F, 3-$CH_3$ phenyl-N($C_2H_5$)($CH_2CH_2CH_2SO_3Na$) | 29 | 550 | + |

TABLE 1-2-continued

| Compound No. | Structural formula | Molecular extinction coefficient (× 10³) | λmax (mn) | Influence of serum components |
|---|---|---|---|---|
| 4 | H₃C, F, C₂H₅, CH₂CH₂COONa substituted aniline | 25 | 550 | + |
| 5 | H₃CO, F, C₂H₅, CH₂CH₂—NH—COCH₃ substituted aniline | 25 | 540 | ++ |

TABLE 1-3

| Compound No. Comparative Example | Structural formula | Molecular extinction coefficient (× 10³) | λmax (mn) | Influence of serum components |
|---|---|---|---|---|
| 1 | F-aniline with C₂H₅ and C₂H₄OH | 15 | 560 | ++ |
| 2 | F-aniline with C₂H₅ and CH₂CH(OH)CH₂SO₃Na | 12 | 555 | ++ |
| 3 | F-aniline with C₂H₅ and CH₂CH₂CH₂SO₃Na | 10 | 555 | ++ |
| 4 | F-aniline with C₂H₅ and CH₂CH₂COONa | 8 | 550 | ++ |
| 5 | F-aniline with C₂H₅ and CH₂CH₂—NH—COCH₃ | 12 | 560 | ++ |

As is clear from the results shown in Table 1-1, Table 1-2 and Table 1-3, the dyes formed from the present inventive compounds had molecular extinction coefficients which were clearly larger than those of the dyes formed from known p-fluoroaniline derivative having no substituents (at both 3- and 5-positions) adjacent to its fluoro group, but were equal to or slightly smaller than those of the dyes formed from known p-fluoroaniline derivatives having a substituent adjacent to its fluoro group at either the 3-position or the 5-position. The dyes formed from the present inventive compound, however, had absorption maximums clearly shifted to a longer wavelength region, as compared with those of the dyes formed from the known p-fluoroaniline derivatives. Moreover, it was substantially free from the slight problem in known p-fluoroaniline derivatives, namely, the fading of the dye by the influence of components present together with an analyte to be measured in a body fluid such as serum which is used as a sample.

EXAMPLE 3

Determination of Hydrogen Peroxide

Reagent solution

A reagent solution was prepared by dissolving the following reagents in 50 mM PIPES-sodium hydroxide buffer (pH 7.0) to predetermined concentrations, respectively.

| | |
|---|---|
| 4-Aminoantipyrine | 0.5 mM |
| Present inventive compound [2] | 0.5 mM |

| | |
|---|---|
| -continued | |
| Peroxidase | 4 U/ml |

Sample

As samples, there were used 1.0, 2.0, 3.0, 4.0 and 5.0 mM hydrogen peroxide solutions prepared by diluting commercially available hydrogen peroxide properly with distilled water.

Procedure

To 3 ml of the reagent solution was added 20 μl of each sample, followed by thorough mixing. The resulting mixture was incubated at 37° C. for 5 minutes, after which absorbance (Es) at 595 nm was measured.

A blank value (EBl) was measured by carrying out the same procedure a above except for using deionized water in place of the sample.

Results

Figure 1:
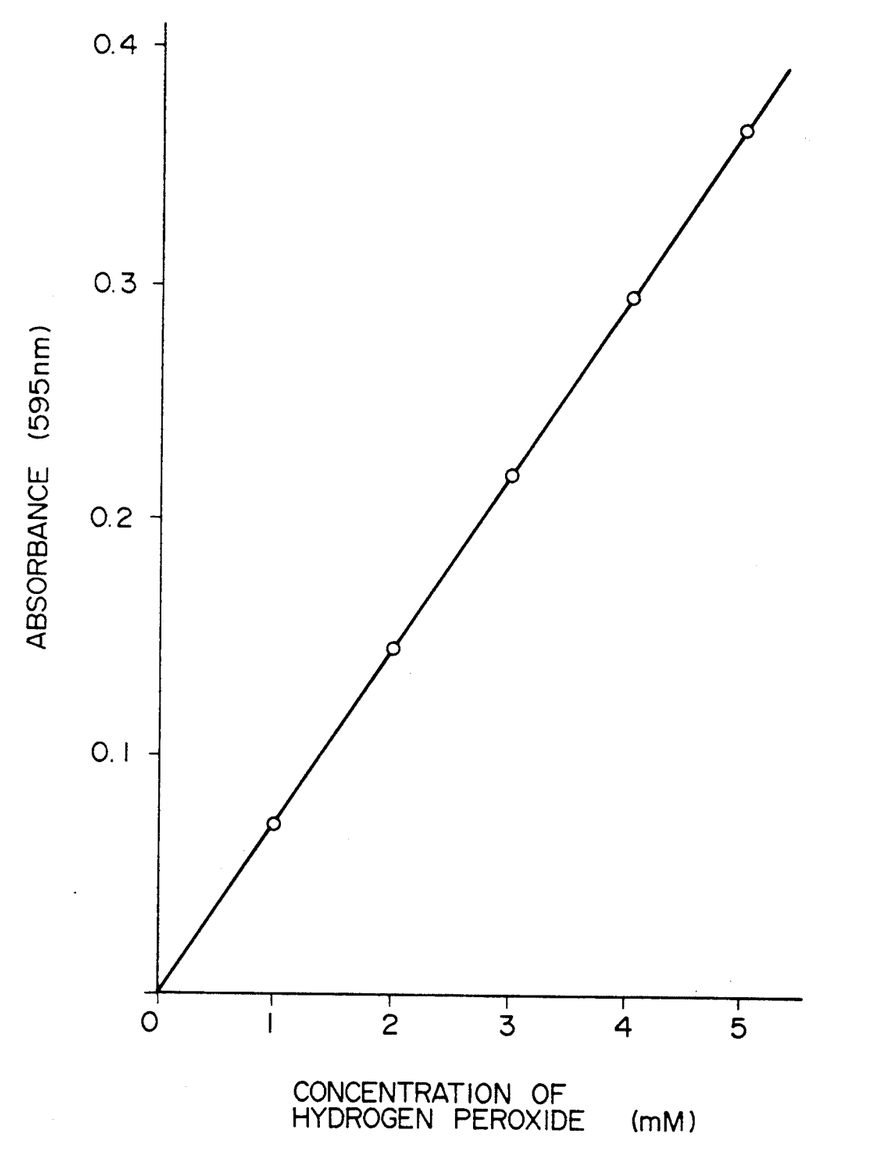
This FIGURE shows a calibration curve in Example 3.

The measurement results are shown in the attached drawing.

As is clear from the attached drawing, a calibration curve obtained by plotting absorbance (Es-EBl) on the axis of ordinate corresponding to individual hydrogen peroxide concentration on the axis of abccissa shows good linearity, indicating that hydrogen peroxide can be quantitatively measured by the process of this invention.

EXAMPLE 4

Investigation of the influence of serum components on coloration stability.

Reagent Solution and Samples

The same reagent solution and samples as in Example 3 were used.

Procedure

To 3 ml of the reagent solution was added 50 μl of normal human serum or deionized water, followed by thorough mixing. Then, 20 μl of each sample was added thereto and thoroughly mixed therewith, and the resulting mixture was incubated at 37° C. for 5 minutes, after which absorbance (Es) at 595 nm was measured.

A blank value (EBl) was measured by carrying out the same procedure as above except for using deionized water in place of the sample.

Results

The measurement results are shown in Table 2.

TABLE 2

| Hydrogen peroxide concentration in a sample (mM) | Additive | |
|---|---|---|
| | Normal human serum | Deionized water |
| | Es-EBl | |
| 1.0 | 0.071 | 0.072 |
| 2.0 | 0.140 | 0.141 |
| 3.0 | 0.214 | 0.215 |
| 4.0 | 0.294 | 0.296 |
| 5.0 | 0.366 | 0.368 | as is clear from Table 2, a dye formed from the p-fluoroaniline derivative of this invention and 4-aminoantipyrine is hardly affected by serum components.

EXAMPLE 5

Determination of Uric Acid

Reagent Solution

A reagent solution was prepared by dissolving the following reagents in 50 mM PIPES-sodium hydroxide buffer (pH 7.0) to predetermined concentrations, respectively.

| | |
|---|---|
| 4-Aminoantipyrine | 0.5 mM |
| Present inventive compound [2] | 0.5 mM |
| Peroxidase | 4 U/ml |
| Uricase | 0.05 U/ml |

Samples

A standard solution containing 10 mg/dl of uric acid and 5 human sera were used as samples.

Procedure

To 3 ml of the reagent solution was added 20 μl of each sample, followed by thorough mixing. The resulting mixture was incubated at 37° C. for 5 minutes, after which absorbance (Es) at 595 nm was measured.

A blank value (EBl) was measured by carrying out the same procedure as above except for using deionized water in place of the sample.

Uric acid concentration in each human serum was calculated by the following equation:

$$\text{Uric acid (mg/dl)} = (Es \text{ obtained for human serum} - EB1) \div (Es \text{ obtained for the standard solution} - EB1) \times 10$$

Results

The results obtained are shown in Table 3.

REFERENCE EXAMPLE 2

Determination of Uric Acid

Using the same samples as in Example 5, uric acid concentration was measured by use of a commercially available kit for measuring uric acid (Uric acid C-Test Wako, mfd. by Wako Pure Chemical Industries, Ltd.).

The results obtained are also shown in Table 3.

TABLE 3

| Human serum No. | Example 5 | Referential Example 2 |
|---|---|---|
| | Uric acid concentration (mg/dl) | |
| 1 | 2.5 | 2.5 |
| 2 | 4.1 | 4.0 |
| 3 | 4.8 | 4.7 |
| 4 | 6.1 | 6.2 |
| 5 | 8.2 | 8.1 |

As is clear from Table 3, the measured values of uric acid obtained by the measuring method of Example 5 using the p-fluoroaniline derivative of this invention as a coupling component of a color producing reagent are in good correlation with those obtained by a conventional method using the commercially available kit.

As described above, this invention provides a novel p-fluoroaniline derivative or a salt thereof which is free from all of problems in compounds conventionally used for the same purpose as in the case of said derivative or salt thereof, for example, the problem that the compounds are not stable in water or a buffer solution containing a surfactant dissolved therein, the problem that a dye formed from the compound had an absorption maximum in a relatively short wavelength region, so that measured values tend to be affected by the influence of components present together with an analyte to be measured in a sample derived from a living body, such as serum, urine or the like, and the problem that the dye formed is decreased in coloration stability (faded) by the influence of components present together with an analyte to be measured in a sample derived from a living body, such as serum, urine or the like. This invention further provides a process for determining the amount of an oxidative substance by using the p-fluoroaniline derivative or salt thereof as a color producing component. Therefore, this invention contributes greatly to the art.

What is claimed is:

1. A p-fluoroanilane derivative represented by the formula [I], or a salt thereof;

wherein $R^1$ and $R^2$ are each $C_2$–$C_4$ alkenyl or $C_1$–$C_5$ alkyl optionally substituted with one or more substituents selected from the group consisting of hydroxy, $C_1$–$C_5$ alkoxy, sulfo, amino, amido, acetamido, propionamido, acyl and acyloxy; $R^3$ and $R^4$ are each $C_1$–$C_5$ alkoxy, $C_2$-14 $C_4$ alkenyl, hydroxyl, halo, sulfo, carboxyl nitro, phenyl, napthyl, tolyl, fluorophenyl, chlorophenyl, bromophenyl, iodophenyl, methoxyphenyl, or hydroxyphenyl, or $C_1$–$C_5$ alkyl optionally substituted by one or more substituents selected from the group consisting of halo and hydroxyl; $R^5$ and $R^6$ are each hydrogen, $C_1$–$C_5$ alkoxy, $C_2$–$C_4$ alkenyl, hydroxyl, halo or $C_1$–$C_5$ alkyl optionally substituted by $C_1$–$C_5$ alkoxy; and $R^1$ and $R^2$ taken together may form a morpholine, piperazine or piperidine ring.

2. A process for determining the amount of an oxidative substance, which comprises using a combination of a main color former and the p-fluoroaniline derivative of the formula [I] or salt thereof of claim 1, as a color producing component, and measuring the change of color produced.

3. A process according to claim 2, wherein the main color former is 4-aminoantipyrine or a derivative thereof.

4. A process according to claim 2, wherein the oxidative substance is hydrogen peroxide.

5. A process according to claim 4, which comprises oxidizing a color producing component in the presence of peroxidase to allow the same to develop a color, and carrying out calorimetric determination on the basis of the coloration thus caused.

6. A process according to claim 4, wherein the hydrogen peroxide is that produced by enzymatic reaction.

7. A process according to claim 6, wherein the hydrogen peroxide is that produced by enzymatic reaction in determination of a trace component in a sample derived from a living body.

8. A process according to claim 7, wherein the determination of a trace component in a sample derived from a living body is determination of a substrate or an enzyme in the sample derived from the living body which is carried out by acting an oxidase on the substrate or a substance produced by enzymatic reaction, and determining hydrogen peroxide produced 9. A process for determining the amount of a peroxidase or heme compound which comprises using a combination of a main color former and the p-fluoroaniline derivative of the formula [I] or salt thereof of claim 1, as a color producing component, and measuring the change of color produced.

10. A process according to claim 9, wherein the main color former is 4-aminoantipyrine or a derivative thereof.

* * * * *